United States Patent [19]

Hirdes

[11] Patent Number: 4,726,769
[45] Date of Patent: Feb. 23, 1988

[54] DENTAL APPLIANCE FOR INTRODUCING A FILLER MATERIAL INTO A TOOTH CAVITY

[76] Inventor: Rudiger Hirdes, Kleinherbeder Strasse 9a, 5810 Witten, Fed. Rep. of Germany

[21] Appl. No.: 921,775

[22] Filed: Oct. 21, 1986

Related U.S. Application Data

[63] Continuation-in-part of Ser. No. 906,918, Sep. 11, 1986.

[30] Foreign Application Priority Data

Sep. 19, 1985 [DE] Fed. Rep. of Germany ....... 3533367
Nov. 8, 1985 [DE] Fed. Rep. of Germany ....... 3539579

[51] Int. Cl.[4] .............................................. A61C 5/04
[52] U.S. Cl. ..................................................... 433/89
[58] Field of Search ........................... 433/89, 90, 164

[56] References Cited

U.S. PATENT DOCUMENTS

| | | | |
|---|---|---|---|
| 532,720 | 1/1895 | Dennis | 433/164 |
| 3,028,672 | 10/1959 | Zandberg | 433/90 |
| 3,221,409 | 12/1965 | Thiel et al. | 433/83 |
| 3,638,314 | 2/1972 | Lopez | 433/90 |
| 3,751,807 | 8/1973 | Noll et al. | 433/89 |
| 3,792,530 | 2/1974 | Smith | 433/83 |
| 3,990,152 | 11/1976 | Hirdes | 433/89 |
| 4,092,778 | 6/1978 | Hirdes | 433/83 |
| 4,306,863 | 12/1981 | Law | 433/83 |
| 4,340,367 | 7/1982 | Vadas et al. | 433/89 |
| 4,377,380 | 3/1983 | Vadas et al. | 433/89 |

Primary Examiner—John J. Wilson
Assistant Examiner—Michael Lynch
Attorney, Agent, or Firm—Michael J. Striker

[57] ABSTRACT

A dental appliance for introducing a filler material into a tooth cavity comprises a support, a filler pipe, a filler expelling element, and a removable magazine which accommodates a filler, and a mechanical transmission which couples the filler expelling element and the magazine expelling element with one another to provide coordination of their movements and includes a toothed rack connected with the magazine expelling element, an expelling lever which is turnably connected with a support and has a free end engaging in the toothed rack and expelling button actuatable by a finger and connected with the filler expelling element, and a projection, the lever being arranged so that during the working stroke it displaces with the toothed rack via the expelling button and the projection in direction toward the filler pipe before a front end of the filler expelling element reaches an end of the opening of the magazine into the filler pipe, a toothed pinion supported in the support, a rotary element connected with the toothed pinion for joint rotation therewith and having a first projection portion for displacing the expelling lever and thereby the toothed rack of the magazine expelling element and a second projection portion for displacing the filler expelling element, a toothed segment supported in the support and engaging with the toothed pinion, the expelling button being formed as a two-arm rotary slider turnably supported in the support and having one arm which is provided with a finger contact portion and extends beyond the support and another arm which has an end articulately engaging the toothed segment.

21 Claims, 3 Drawing Figures

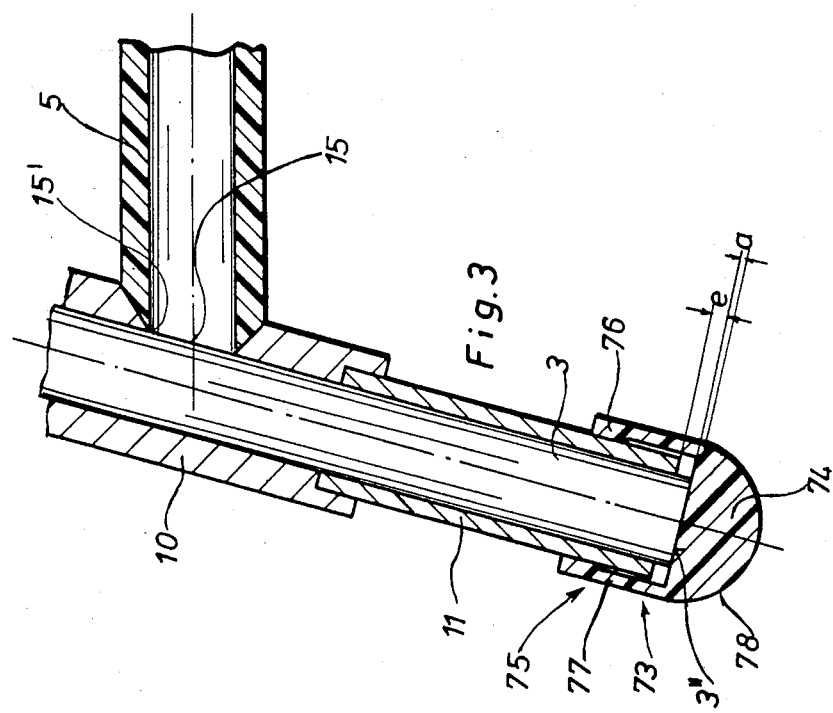
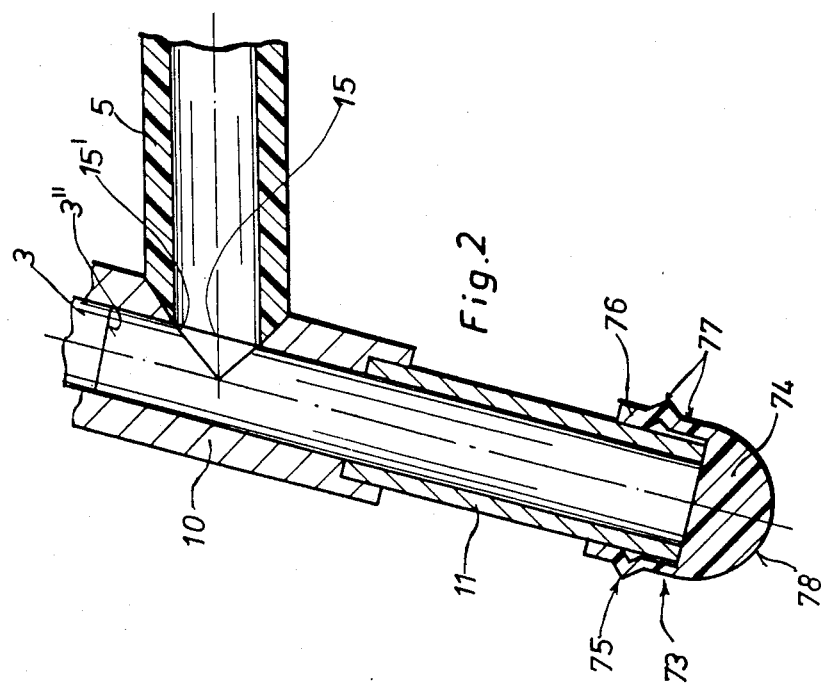

DENTAL APPLIANCE FOR INTRODUCING A FILLER MATERIAL INTO A TOOTH CAVITY

CROSS-REFERENCE TO A RELATED APPLICATION

This application is a continuation-in-part of U.S. patent application Ser. No. 906,918 filed on Sept. 11, 1986 of the same inventor.

BACKGROUND OF THE INVENTION

The present invention relates to a dental appliance for introducing a filler material into tooth cavities.

More particularly, it relates to a dental appliance which has a filler pipe, a filler expelling element which is reciprocable in a first passage and merges into the filler pipe, a replaceable magazine which extends transversely to the filler pipe and opens into the latter so that a part of the filler material such as amalgam is pressed from the magazine via a second passage by a magazine expelling element in a working stroke which starts above the opening of the magazine and ends at the outlet of the filler pipe, so as to press the part of the filler material into the filler pipe. A mechanical transmission couples the filler expelling element and the magazine expelling element surrounded by a common housing so as to coordinate their movements. The transmission includes a toothed rack which is connected with the magazine expelling element, an expelling lever which is turnably connected with the housing and has a free end engaging in the toothed rack, an expelling button which is actuatable by a finger and connected with the filler expelling element, and a projection. The lever is arranged so that during the working stroke it displaces with the toothed rack via the expelling button and the projection in direction toward the filler pipe before the front end of the filler expelling element reaches at the upper end of the opening of the magazine into the filler pipe. This dental appliance is disclosed in the above identified U.S. patent application.

In the above described dental appliance, the fingeractuatable expelling button moves always parallel with and relative to the filler expelling element. This means that a pure translatory movement is possible, which is performed by the forward and rearward stroke of the finger of the operator, for example by the indicating finger.

It has been found that under certain conditions it can be not favorable ergonomically when the operator in addition to the required translatory movement of the filler expelling element with the finger, performs a pressing movement upon the expelling button.

SUMMARY OF THE INVENTION

Accordingly, it is an object of the present invention to provide a dental appliance which is improved as compared with the above described appliance, in the sense of ergonomical actuation of the dental appliance.

In keeping with these objects and with others which will become apparent hereinafter, one feature of the present invention resides, briefly stated, in a dental appliance in which the expelling button is formed as a two-armed rotary slider supported turnably in the housing and having one arm provided with a finger contact portion and extending outside the housing and another arm supported in the housing and articulately engaging a toothed segment whose teeth engage with a toothed pinion fixedly connected with a rotary element for joint rotation therewith, and the rotary element has a first projecting portion for displacing the expelling lever and therefore the toothed rack of the magazine expelling element and a second projecting portion for displacing the filler expelling element.

When the dental appliance is designed in accordance with the above features the operator by means of its indicating finger can apply a pressing movement upon the two-arm rotary slider to cause a circular arcuate displacement and this circular arcuate displacement, by means of the above described transmission, is converted into a translatory movement of both the magazine expelling element and the filler expelling element and simultaneously coordinates these movements. It is also guaranteed here that the magazine expelling element presses the desired small amalgam portion without hardening into the filler pipe at a time point, when the filler expelling element just starts its working stroke, but does not reach the upper edge of the opening of the magazine into the filler pipe. Thereby the discharge of a small, insignificant amalgam portion into the filler pipe without pressure forces which can release hardening is not prevented.

In accordance with another advantageous feature of the present invention, the rotary element is formed as a disc whose first projecting portion is formed as a peripheral cam surface and whose second projecting portion is formed as a circular arc toothed portion engaging with a toothed strip which is mounted on the filler expelling element. In this case, in accordance with the above mentioned application, the expelling lever is formed as a flat spring which with its one end is immovably fixed in the housing and its free end engages into the toothed rack of the magazine expelling element and displaces the same under the action of the first projecting portion formed as the cam surface.

The rotary element and the toothed pinion are advantageously arranged on the same pivot axle on which the two-arm rotary slider is arranged. The toothed pinion is connected with the rotary element relatively non-rotatably. Therefore, for all these three parts only one pivot axle is required. The second pivot axle is required however for the toothed segments supported in the housing.

The circular arc toothed portion of the rotary element disengages from the toothed strip of the filler expelling element advantageously when the filler expelling element is in its extreme position and a vibrator acts upon the filler expelling element. Thereby in the sense of the vibration process, no disadvantageous vibration forces are transmitted from the filler expelling element to the teeth of the circular arc toothed portion, to the toothed strip, the pinion and the toothed segment.

In accordance with a further advantageous feature of the present invention, the two-arm rotary slider is engaged by a return spring which turns back the rotary slider with simultaneous pulling back the filler expelling element to its initial position. Thereby, with improvement of the ergonomical condition, the operator has only to apply a pressure force upon the turning slider during displacement of the filler expelling element and magazine expelling element. The return spring serves for pulling back of the filler expelling element and for turning back of the two-arm rotary slider.

During compacting of the filler material by means of a vibrator described in the above mentioned patent application, the edge of the tooth cavity can be damaged by the end of the filler expelling element which is always composed of metal, and also by the surrounding filler pipe which is also composed of metal. For preventing this and guaranteeing a uniform condensing of the amalgam portions, a plug sleeve is fitted onto the end of the filler pipe after filling of the tooth cavity, and can be removed by hand after finishing the forming and compacting. The plug sleeve can be fitted in a force-transmitting and/or formlocking manner and composed of a material which is softer than the tooth enamel. The plug sleeve can have at its one end a firmly closed plug core, on which the filler expelling element acts during the compacting. The other end of the plug sleeve can be formed as a holding ring which elastically surrounds the filler pipe. The holding ring can be provided at its one end with a clamping ring and at its other end which faces toward the plug core with a longitudinally-changeable expansion ring. The vibration impacts of the end of the filler expelling element applied to the plug core allow the longitudinal expansion without releasing the clamping ring from the outer periphery of the plug sleeve.

It is especially advantageous when the plug sleeve is composed of a rubber with a suitable shore hardness or of synthetic plastic material, for example, of polyamide or polyolefine, and the outer surface of its plug core have different configurations in form of a sphere, a rounded cone, an ellipsoid or a rounded cylinder. In this case by fitting of the respectively shaped plug sleeve over the end of the filler pipe, the plug which is optimal for the shape of the tooth cavity can be momentarily arranged on the new filling appliance and can be momenarity removed immediately after its use.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 2 is a view showing a fragment II in FIG. 1, on an enlarged scale, and showing a plug sleeve which is fitted in a working phase of a filler expelling element on a free end of a filler pipe; and FIG. 3 is a view substantially corresponding to the view of FIG. 2, but showing the dental appliance in the position in which during vibration the end of the filler expelling element extends outwardly beyond the end of the filler pipe.

DESCRIPTION OF THE PREFERRED EMBODIMENTS

Figure 1:
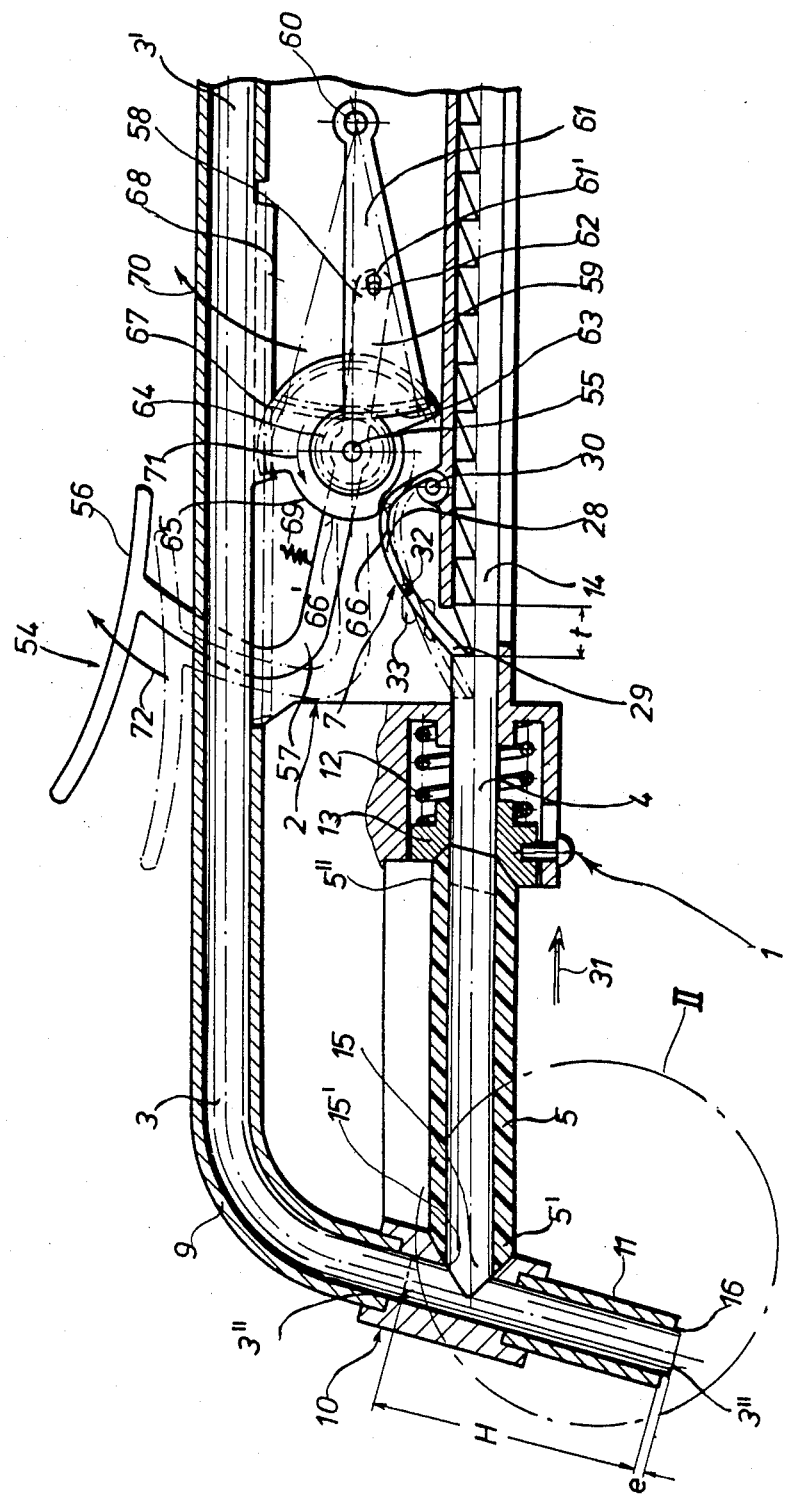
FIG. 1 is a partially sectioned view of a dental appliance in accordance with the present invention, with an expelling lever formed as a flat spring.

A dental appliance for introducing a filler material into tooth cavities in accordance with the present invention is identified with reference numeral 1 and includes a housing 2, an expelling element for a filler material 3, a magazine expelling element 4, an easily exchangeable magazine 5, a finger actuated expelling button 1 which in this case is formed as a rotary slider 54, and an expelling lever 7 in form of a flat spring 28.

The flat spring 28 has one end 30 which is immovably mounted in the housing 2, and another free end 29 which engages into a toothed rack 14 at the rear extension of the magazine expelling element 4.

The filler expelling element 3 is reciprocably movable in a guiding passage 9. A filler pipe 10 with an exchangeable tamping end member 11 is connected with the guiding passage 9. The magazine 5 opens with its front end 5' into the filler pipe 10. The magazine 5 is pressed under the action of a spring 12 acting against its other end 5'', against the filler pipe 10 and during the working phase of the device is held by the spring.

A cylindrical coulisse block 13 is arranged between the magazine 5 and the spring 12 in a slidingly displaceable manner. It is provided with a respectively shaped surface at its end which faces toward the magazine 5 for its insertion.

The toothed rack 14 on the rear extension of the magazine expelling element 4 together with the expelling lever 7 formed as the flat spring 28 are parts of a transmission which coordinates and couples with one another the movements of the filler expelling element 3 and magazine expelling element 4, when the filler expelling element 3 performs a working stroke h which starts above an inlet opening 15 of the magazine 5 and finishes at an outer opening 16 of the filler pipe 10. In the event of vibrations applied to the filler expelling element 3, the working stroke is extended by the expelling path e of the vibrator.

In accordance with the embodiment shown in FIG. 1, the expelling button includes a rotary slider 54 which is supported in the housing 2 by means of a pivot axle 55. The rotary slider 54 has an arm 57 which extends outwardly beyond the housing 2 and is provided with a finger contact member 56 formed with a depression for a finger. Another arm 59 of the rotary slider 54 engages with its end 58 a toothed segment 61 which is pivotably supported on an axle 60 in the housing 2. The engagement of the arm 59 with the toothed segment 61 is performed by means of a pin 62. Teeth 63 of the toothed segment 61 engage with a toothed pinion 64 which is also supported on the axle 55. A rotary element 65 is connected with the toothed pinion 64 fixedly for joint rotation therewith and is also rotatably supported on the axle 55. This rotary element 65 includes a disc and is provided with a projection 66 which is formed as a cam surface for displacing the lever 28 and thereby the toothed rack 14 of the magazine expelling element 4. The rotary element 65 further has a second projection in form of a circular arc toothed portion 67. The latter engages with a toothed strip 68 mounted on the rear end of the filler expelling element 3. Thereby during a rotation of the circular arc toothed portion 67, the filler expelling element 3 can be displaced in a counterclockwise direction.

When the filler expelling element 3 is displaced to its extreme position e, and a not shown vibrator acts on its rear end, the circular arc toothed portion 67 of the rotary element 65 disengages from the toothed strip 68 of the filler expelling element 3. Thereby vibration forces are eliminated, which otherwise can act via the circular arc toothed portion 67 of the rotary element upon the teeth of the pinion 64 and thereby upon the teeth 63 of the toothed segment 61.

A return spring 69 engages the arm 57 of the rotary slider 54 and turns it back with simultaneous pulling of the filler expelling element 3 to its initial position shown in FIG. 1. The rotary slider 54, the pinion 64, and the rotary element 65 are supported on the same axle 55, however, only the pinion 64 and the rotary element 65 are connected immovably relative to one another.

While in FIG. 1 the expelling lever is formed as a flat spring 28, it can also be formed as an expelling crank as shown in FIGS. 4–7 of the above mentioned U.S. patent application filed on Sept. 11, 1986.

The above device shown in FIG. 1 operates in the following manner:

When by means of the finger contact member 56 the rotary slider 54 is pressed from its position shown in solid lines to its position shown in broken lines, the lever arm 59 with its pivot pin 62 engaging in an elongated hole 61' of the tooth segment 61 turns the toothed segment 61 in direction of the arrow 70. Thereby the pinion 64 and simultaneously the rotary element 65 coupled with the pinion in rotatable manner is caused to rotate in direction of the arrow 71 via a first projection formed as a cam surface 66 on the rotary element 65, the flat spring 28 is pressed down to its position shown in broken lines and displaces the toothed rack 14. As a result of this, the magazine expelling element 4 presses an amalgam portion from the magazine 5 into the filler pipe 10. During a return turning of the cam surface 66 in a direction opposite to the arrow 71, the flat spring 28 is spring-biased under the action of its own tensioning by at least one tooth pitch t back to its initial position, from which it can be forced by the cam surface 66 to a new stroke.

In the position shown in FIG. 1, the front end 3" of the filler expelling element 3, is located first above the upper edge 15' of the inlet opening 15 of the magazine in the filler pipe 10. By pressing down of the rotary slider 54 from its position shown in solid lines to its position shown in broken lines, simultaneously via the pinion 64 the rotary element 65 which is connected with the pinion for rotation therewith is rotated in direction of the arrow 71. Thereby, the filler expelling element 3 is displaced, via the circular arc toothed portion 67 and the toothed strip 68, in direction toward the upper edge 15' of the inlet opening 15 of the magazine 5. When the front end 3" of the filler expelling element 3 reaches the upper edge 15', the insertion of the amalgam portion by the magazine expelling element 4 into the filler pipe 10 finishes. When the amalgam portion is cut off by the further withdrawing end 3" of the filler expelling element 3 and supplied through the outlet 16 of the filler pipe 10 into a not shown tooth cavity.

Since a circular arc surface 66' is connected with the cam surface 66 at the same distance from the pivot axle 55 and remains constant, the magazine expelling element 4 remains during the above described displacement of the filler expelling element 3 in the position which is determined by the brokenline position of the flat spring 28.

With releasing of the rotary slider 54, the spring 69 pulls the rotary slider 54 in direction of the arrow 72 to its initial position. Thereby, the pinion 64 and the rotary element 65 are withdrawn in direction opposite to the arrow 71 to its initial positions, via the lever arm 59, the coupling pin 62, the toothed segment 61 and the teeth 63.

Thereby via the toothed strip 68, the filler expelling element 3 is also withdrawn to the shown initial position, so that a new displacement of the filler expelling element 3 can be released by acting upon the finger contact member 56 and thereby the rotary slider 54.

When the front end 3" of the filler expelling element 3 is displaced to its extreme position e extending beyond the filler pipe 10, a not shown vibrator can act upon the rear end 3' of the filler expelling element 3. In this case the circular arc toothed portion 67 advantageously disengages from the toothed strip 68, so that disadvantageous vibration forces are not applied either upon the teeth of the circular arc toothed portion 67 and thereby the toothed strip 68, or upon the teeth of the pinion 64 and thereby the teeth 63 of the tooth segment 61.

For withdrawing the toothed rack 14 for the purpose of exchanging the magazine 5 in direction of the arrow 31, the flat spring 28 must be pulled out of the toothed rack 14. This is performed in that the flat spring 28 is provided with an arresting projection 32. The projection 32 engages in a substantially Z-shaped opening of the housing 2 and is formed so that the flat spring 28 can be disengaged from the teeth of the toothed rack 14 from outside by means of a finger. This disengaging possibility must be provided at any time, in order to prevent a repeated amalgam displacement of the magazine expelling element 4 during premature return turning of the rotary slider 54 prior to the cutting off of the amalgam portions. The magazine 5 is displaced against the force of the spring 12 in direction of the arrow 31, and then a front end 5' extends downwardly beyond the filler pipe 10 and so then the rear end 5" can be withdrawn from the cylindrical coulisse block 13. After this, the new filled magazine 5 is inserted in a reverse order, and then the flat spring 28 is brought by means of the arresting projection 32 again in engagement with the teeth of the toothed rack 14.

After filling of the not shown tooth cavity, a plug sleeve 73 is fitted onto the free end of the filler pipe 10 or over a plug end 11. The plug sleeve 73 is composed of a material which is softer than the teeth enamel. After the end of the forming and compacting process, the plug sleeve is removed by hand from the filler pipe or the plug end. The plug sleeve is provided on its one end with a firmly closed plug core 74 upon which the front end 3" of the filler expelling element 3 acts during the compacting process. A holder 75 is provided on the other end of the plug sleeve and elastically engages the end 11 of the filler pipe 10. The holder 75 has a clamping ring 76 at its free end. It is also provided with a longitudinally changeable expansion ring 77 at its end facing toward the plug core 74. The plug sleeve 73 is composed of rubber or synthetic plastic material, for example, polyamide or polyolefine. The plug core 75 can have an outer surface 78 which can be provided with different configurations corresponding to different shapes of tooth cavities. It can be formed as a sphere, a rounded cone, an ellipsoid or a rounded cylinder.

In the examples shown in FIGS. 2 and 3, the outer surface of the plug core 74 has a semi-spherical shape.

As long as the front end 3" of the filler expelling element 3 is displaced in accordance with FIG. 3 to its extreme position e, and the rear end 3' (see FIG. 1) of the filler expelling element 3 is acted upon by a not shown vibrator, the expansion ring 77 is brought into action. As a result of it, the clamping ring 76 maintains its unchanged position on the plug end 11 of the filler pipe 10, while the plug core 74 vibrates for example with the amplitude a in both direction of the double arrow 79. With its semi-spherical outer surface 78, the plug core 74 compresses and compacts the amalgam. Simultaneously during these vibrations, the neighboring edges of the teeth enamel of the respective toothed cavity are protected.

It will be understood that each of the elements described above, or two or more together, may also find a useful application in other types of constructions differing from the types described above.

While the invention has been illustrated and described as embodied in a dental appliance for introducing a filler material into a tooth cavity, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A dental appliance for introducing a filler material into a tooth cavity, comprising a support; a filler pipe; means forming a first passage; a filler expelling element reciprocably movable in said first passage, said filler expelling element merging into said filler pipe and having a front end; a removable magazine which accommodates a filler and a plurality of portions of which can be expelled therefrom, said magazine extending transversely to said filler pipe and opening into the latter, said magazine having an inlet opening which opens into said filler pipe and is provided with an upper edge; a second passage; a magazine expelling element guided in said second passage for pressing a portion of the filler from said magazine into said filler pipe, said filler expelling element and said magazine expelling element being surrounded by said support; mechanical transmission means which couple said filler expelling element and said magazine expelling element with one another to provide coordination of their movements, said transmission means including a toothed rack which is connected with said magazine expelling element, an expelling lever which is turnably connected with said support and having a free end engaging in said toothed rack and an expelling button which is actuatable by a finger and connected with said filler expelling element, and a projection, said lever being arranged so that during the working stroke it displaces with said toothed rack via said expelling button and said projection in direction toward said filler pipe before said front end of said filler expelling element reaches said other end of said opening of said magazine into said filler pipe; a toothed pinion supported in said support; a rotary element connected with said toothed pinion for joint rotation therewith and having a first projecting portion for displacing said expelling lever and thereby said toothed rack of said magazine expelling element and a second projecting portion for displacing said filler expelling element; a toothed segment supported in said support and engaging with said toothed pinion, said expelling button being formed as a two-arm rotary slider turnably supported in said support and having one arm which is provided with a finger contact portion and extends beyond said support and another arm which has an end articulately engaging said toothed segment.

2. A dental appliance as defined in claim 1, wherein said rotary element is formed as a disc, said first projecting portion of said rotary element being formed as a cam surface, said second projecting portion of said rotary element being formed as a circular arc toothed portion; and further comprising a toothed strip mounted on said filler expelling element and engaging with said circular arc toothed portion.

3. A dental appliance as defined in claim 1; and further comprising a pivot axle supporting said two-arm rotary slider, said rotary element and said toothed pinion being also supported on said pivot axle, said toothed pinion being connected with said rotary element non-rotatably relative to one another.

4. A dental appliance as defined in claim 2, wherein said filler expelling element is movable to its extreme position, said circular arc toothed portion of said rotary element being formed so that in the extreme position of said filler expelling element it disengages from said toothed strip of said filler expelling element.

5. A dental appliance as defined in claim 1; and further comprising a return spring which engages said two-arm rotary slider so as to bring the latter to its initial position with simultaneous pulling back of said filler expelling element.

6. A dental appliance as defined in claim 1, wherein said expelling lever is formed as a flat spring.

7. A dental appliance as defined in claim 1, wherein said filler pipe has a free end through which a filler is filled into a tooth cavity; and further comprising a plug sleeve which is fittable onto said free end of said filler pipe in a force-transmitting member and removable by hand after finishing of forming and compacting the filler in the tooth cavity, said plug sleeve being composed of a material which is softer than tooth enamel.

8. A dental appliance as defined in claim 7, wherein said plug sleeve is fittable on said end of said filler pipe in a force-transmitting manner.

9. A dental appliance as defined in claim 7, wherein said plug sleeve is fittable on said end of said filler pipe in a form-locking manner.

10. A dental appliance as defined in claim 7, wherein said plug sleeve has a first closed end provided with a plug core upon which said filler expelling element acts during the compacting.

11. A dental appliance as defined in claim 10, wherein said plug sleeve has another end which is provided with a holding ring elastically embracing said filler pipe.

12. A dental appliance as defined in claim 11, wherein said holding ring has a free end which is provided with a clamping ring, and another end which is provided with a length-changeable expansion ring.

13. A dental appliance as defined in claim 7, wherein said plug sleeve is composed of rubber.

14. A dental appliance as defined in claim 7, wherein said plug sleeve is composed of a synthetic plastic material.

15. A dental appliance as defined in claim 14, wherein said plug sleeve is composed of a synthetic plastic material selected from the group consisting of polyamide and polyolefine.

16. A dental appliance as defined in claim 10, wherein said plug core of said plug sleeve has an outer surface shaped as a sphere.

17. A dental appliance as defined in claim 10, wherein said plug core of said plug sleeve has an outer surface shaped as a rounded cone.

18. A dental appliance as defined in claim 10, wherein said plug core of said plug sleeve has an outer surface shaped as an ellipsoid.

19. A dental appliance as defined in claim 10, wherein said plug core of said plug sleeve has an outer surface shaped as a rounded cylinder.

20. A dental appliance as defined in claim 1; and further comprising a vibrator which acts upon said filler expelling element.

21. A dental appliance as defined in claim 1, wherein said expelling lever is formed as an expelling crank.

* * * * *